Figure 1:
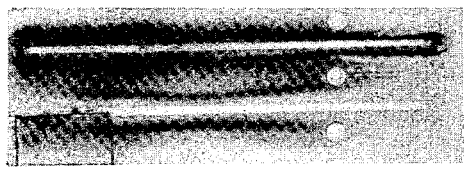

United States Patent [19]

Osther et al.

[11] 4,273,703

[45] Jun. 16, 1981

[54] INTERFERON PRODUCT AND PROCESS FOR ITS PREPARATION

[75] Inventors: Kurt B. Osther, Naerum; Werner K. Jensen, Roskilde, both of Denmark

[73] Assignee: Ess-Food Eksport-Svineslagteriernes Salgsforening, Copenhagen, Denmark

[21] Appl. No.: 955,389

[22] Filed: Oct. 27, 1978

[30] Foreign Application Priority Data

Nov. 1, 1977 [DK] Denmark .............................. 4859/77

[51] Int. Cl.³ ...................... A61K 45/02; A61K 37/00; C07G 7/00
[52] U.S. Cl. .................................. 260/112 R; 424/85
[58] Field of Search ....................... 424/85; 260/112 R

[56] References Cited

PUBLICATIONS

Chemical Abstracts, vol. 77 (1972), p. 111830e–111831f.
Mogensen et al., "Pharm. Ther. A.," vol. 1 (1977), p. 369–381.
Gresser et al., "Nature," vol. 251 (1974), p. 543–545.
Toneva, Venera, Proc. of 3rd Int. Pig Veterinary Society Congress, Lyon (1974).
Chem. Abstr., vol. 73, 33425c (1970).
Chem. Abstr., vol., 71, 68903t (1969).
Chem. Abstr., vol. 78, 122444d (1973).
Chem. Abstr., vol. 72, 10984z (1970).
Microb. Abstr., Section A, vol. 8, No. 7, 90–91 8A5062 (1973).
Chem. Abstr., vol. 78, 68982n (1973).

*Primary Examiner*—Delbert R. Phillips
*Assistant Examiner*—Blondel Hazel
*Attorney, Agent, or Firm*—Hubbell, Cohen, Stiefel & Gross

[57] ABSTRACT

Exogenic porcine interferon for administration in human beings. The porcine interferon shows antiviral protecting activity on cultured human cells and is substantially free of any immunoelectrophoresis bands which are not identical or partially identical with bands in human leucocyte interferon or human agammaserum. A process for preparing the porcine interferon by harvesting, isolating and, if desired, priming porcine leucocytes, treating them with an interferon inductor and incubating them and obtaining the interferon formed, the process being characterized in using, as added protein source in any of the said stages, a source which is substantially free of immunoelectrophoresis band which are not identical or partially identical with bands in human agammaserum.

4 Claims, 9 Drawing Figures

INTERFERON PRODUCT AND PROCESS FOR ITS PREPARATION

The present invention relates to a particular class of interferons and a process for the preparation thereof.

Interferons are proteins which are produced by certain living cells when the cells are induced with various types of virus and with certain synthetic substances. Interferons are released from cells and protect other cells against viral infections (Glasgow, L. A., Interferon: A Review., J. Pediat. 67: 104, 1965; Ho, M., Interferons. New Engl. J. Med., 266: 1258-1264, 1313-1318 and 1367-1371, 1962; Merigan, T. C., Winget, C. A. and Dixon, C. B., Purification and Characterization of Vertebrate Interferons; J. Molec. Biol., 13: 679-686, 1965; Wagner, R. R., Interferon. A Review and Analysis of Recent observations. Americ. J. Med., 38: 726-737, 1965).

It has been shown that interferons may be induced in various animal cells, including leucocytes. Human leucocytes are considered good interferon-producers. These cells may be used for preparing exogenic interferon (Cantell, K., Hirvonen, S., Mogensen, K. E. and Pyhälä, L., Human Leukocyte Interferon: Production, Purification, Stability and Animal Experiments., Proceedings of a Tissue Culture Association Workshop, May 1973, 35-38), but human leucocytes are only available in limited amounts (from donor blood). The antiviral, and thereby cell-protecting, function of interferons is not particularly species-specific. For example, human leucocyte interferon protects, in vitro, cultivated cells from various non-primates such as cows, pigs, etc. (Gresser, I. Bandu, M. T., Brouty-Boyé, D. and Tovey, M. G., Pronounced Antiviral Activity of Human Interferon on Bovine and Porcine Cells., Nature, London, 251: 543-545, 1974). The interferon production by bovine skin fibroblasts and porcine kidney cells could only to a small degree or not at all show interferon activity on human cells. In contrast to human leucocyte interferon, human fibroblast interferon showed less antiviral effect on cultured bovine and porcine cells. In vitro, bovine interferon has antiviral effect on human cells (Tovey, M. G., Bandu, M. T., Begon-Lours, J., Brouty-Boyé, D. and Gresser, I., Antiviral Activity of Bovine Interferons on Primate Cells., J. Gen. Virol., 36: 341-344, 1977).

The clinical interest in interferon is also due to the fact that in addition to the possibilities of treating virus diseases, interferon offers a wide spectrum of possibilities of treating cancer diseases (Cantell, K., Prospects for the Clinical Use of Exogenous Interferon., Medical Biology, 55: 69-73, 1977, Strander, H., Cantell, K., Ingimarsson, S. and Jakobsson, P. A., Interferon Treatment of Osteogenic Sarcoma: A Clinical Trial, Fogarty Int. Center Proc. Wash. D.C., 28: 377-381, 1977). The fact that only relatively few treatments have been performed so far is due to the limited production of human leucocyte interferon, the limitation being imposed by the number of blood donors.

For the preparation of interferon in larger scale, various workers have started using lymphoblastoid cells (for example Namalva cell lines) which are characterized by their capability of continuously dividing themselves and producing interferon, and which are of malignant origin (Strander, H., Mogensen, K. E. and Cantell, K., Production of Human Lymphoblastoid Interferon., J. Clin. Microbiol., 1: 116-117, 1975).

Furthermore, it has been attempted to produce fibroblast interferon by inducing cultured human fibroblasts in several passages (Merigan, T. C., Discussion, In: Interferon, eds. G. E. W. Wolstenholme and M. O'Connor (J. & A. Churchill, London, 1968, p. 70). The disadvantage of this type of production is partly that the fibroblasts are capable of growing only in monolayer culture and not in suspension cultures, thus resulting in a relatively small yield, and partly that the fibroblasts can only be employed through relatively few passages.

According to the present invention, sufficient amounts of interferon may be prepared in a suitable and economic way by using, as the interferon-producing cells, porcine leucocytes, that is leucocytes from pigs. According to the invention it has been found that porcine leucocytes produce interferon which show antiviral protecting activity on human cells, both on primary cell lines and on continuous cell lines, and that the purified interferon preparations prepared from the porcine leucocytes are tolerated by human beings upon parenteral administration, even after administration of booster dose. This indicates that porcine leucocyte interferon will be useful as a valuable substitute for human interferon for the several uses for which human interferon has been found to be indicated (compare, for example, the references cited above), including treatment of diseases such as virus diseases and cancer diseases in human beings, for prophylaxis together with any form of immunosuppressive treatment, for example also in such treatment when used in connection with transplantation, etc., and that this substitute can be available in very considerable amounts. In addition, the porcine leucocyte interferon is, of course, indicated for treatment of viral diseases in pigs and other non-primates and, in human beings, pigs, and other non-primates, for treatment of diseases induced by an intracellular microbe such as Rickettsia.

In addition, the porcine leucocyte interferon may be useful for various purposes in vitro or as a reagent, for example for scientific investigations and as priming interferon in the preparation of interferon.

It has been described in the literature that porcine leucocytes and other pig cells are capable of producing interferon, cf. for example Toneva, V., Study on the Production and Qualities of Interferons Obtained from Porcine White Blood Cells Using Various Viruses as Inductors, Proceed. of 3rd Int. Pig Veterinary Society Congress, Lyon, June 12-14, 1974. Vengris, V. E. & Maré, C. J., Swine Interferon I. Induction in Porcine Cell Cultures with Viral and Synthetic Inducers, Can. J. comp. Med., 36: 282-287, 1972, Richmond, J. Y. An Interferon-Like Inhibitor of Foot-and-Mouth Disease Virus Induced by Phytohemagglutinin in Swine Leukocyte Cultures. Arch. ges. Virusforsch., 27: 282-289, 1969, Richmond, J. Y., Interferon of Foot-and-Mouth-Disease Virus: A New Assay for Interferon. Arch. ges. Virusforsch., 30: 75-81, 1970. These references deal with the inhibitory (antiviral) effect of the interferon on virus diseases which attach animal cells, and in these references, several types of virus and several types of synthetic inductors are used for induction of interferon in porcine leucocyte cultures. However, none of these references disclose that porcine leucocyte interferon shows antiviral protecting activity on human cells, neither do they disclose the preparation of a porcine leucocyte interferon preparation which could properly be used in human beings.

In order that the porcine leucocyte interferon may be properly used in human beings, it should not give rise to hypersensitivity reactions upon parenteral administration in human beings, and according to the present invention this is obtained in that both during the preparation of the porcine leucocytes for the interferon production and during the very interferon production procedure, any addition of proteins which might give rise to hypersensitivity reactions in human beings is avoided, which, according to the invention, is solved in practice by using, as protein sources for the media employed, protein sources which in immunoelectrophoreses are substantially free of bands which are not identical or partially identical with bands in human agammaserum when antitotal human serum protein, antihuman IgG, antihuman IgA, antihuman IgM and antihuman albumin is used as precipitating antibody (the term "agammaserum" is intended to designate serum which has been depleted of the gammaglobulin fraction, for example by removal by salt precipitation). This requirement to the protein source is fulfilled by human agammaplasma and (of course) human agammaserum and fractions thereof, including human albumin and human hemoglobin from hemolyzed erthrocytes (the hemoglobin will substantially not show bands against the above antibodies). However, according to the invention it is of special importance that the above-mentioned requirement is also fulfilled by the corresponding porcine materials, including porcine agammaplasma or agammaserum or fractions of such agammaserum, including especially porcine albumin, and by porcine hemoglobin from hemolyzed erythrocytes. The fact that porcine protein sources show this identity with human protein materials is utilized in a further aspect of the present invention which is described in greater detail below. The measure of using, as added protein source, only a source which shows the above identity with human agammaserum, is in contrast to the known art in which protein sources of a character not tolerable by human beings, such as foetal calf serum or total porcine serum have been used in the incubation of non-primate cells.

Apart from the fact that it shows the properties generally stated for interferon in the literature, including that it is pH stable, non-dialysable, sensitive to trypsin, non-sedimentable, relatively heat stable and shows broad-spectred antiviral activity, the porcine leucocyte interferon prepared with utilization of the above-stated measures which are characteristic to the present invention, may be characterized in that it shows protecting antiviral activity on human cells in culture and that, in immunoelectrophoresis, it is substantially free of bands which are not identical or partially identical with bands in human leucocyte interferon or human serum when using, as precipitating antibody, antitotal human serum protein, antihuman IgG, antihuman IgA, antihuman IgM and antihuman albumin and antihuman leucocyte interferon produced in sheep using human leucocyte interferon prepared as described by K. E. Mogensen and Karl Cantell (Pharmac. Ther. A., Vol. 1, pp 369–381, 1977), apart from any bands originating from the medium in which the interferon inductor (when this is a biological material) has been propagated. In other words, this means that in immunoelectrophoresis, the porcine leucocyte interferon according to the invention shows identity with the human leucocyte interferon prepared according to K. E. Mogensen and Kari Cantell (Pharmac. Ther. A., Vol. 1, pp 369–381, 1977), apart from any bands originating from the medium in which a biological interferon inductor has been propagated. Hence, there must be such a great similarity between human interferon and porcine interferon that the human cells show receptors for porcine interferon, compare the values stated in Example 4 of the titer of the porcine interferon determined in human cell cultures.

Figure 9:
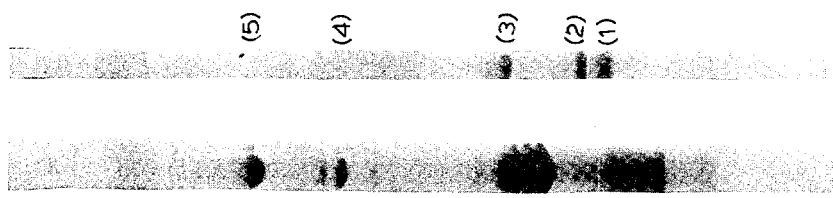
Figure 8:
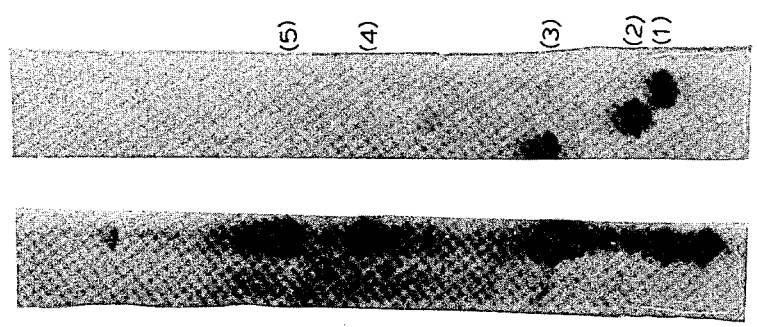
Figure 7:
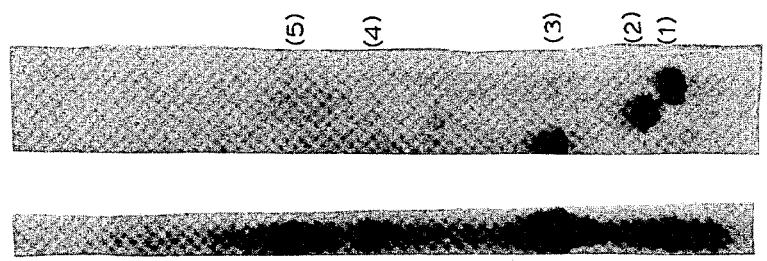

The great similarity between human leucocyte interferon and porcine leucocyte interferon is also apparent from the results of polyacrylamide gradient gel electrophoresis which substantially show identical bands, cf. FIGS. 7–9 with the appertaining explanation.

As appears from Example 5, it seems that with respect to its antiviral protecting activity on human cells in culture, porcine interferon is partially neutralized by antihuman leucocyte interferon prepared in sheep.

In accordance with common practice, the term "interferon" in the present specification and claims is intended to designate not only the proportion of "interferon molecules" in the product, but also the accompanying proteins which, with the present technical standard, it has not yet been possible to remove completely, and the complete removal of which may be not even advantageous, especially not as far as the albumin part of the product is concerned. In addition to crude interferon, which, in practice, is the culturing or incubation medium in which the interferon is produced in the interferon preparation, the following product types are of interest within the interferon technique:

"Concentrated crude interferon", which is a product usually prepared from the culturing or incubation medium by neutralization of inductor virus at pH 2 and potassium thiocyanate precipitation at pH 3.5. The abbreviation for this type of interferon is usually "CIF". CIF contains a considerable amount of accompanying proteins and usually shows relatively low stability and relatively high immunogenicity.

"Partially purified interferon" ("PIF"), which is a product that is considerably less contaminated with accompaying protein and which, per volume unit, contains a much higher interferon activity. PIF may typically be prepared from crude interferon by potassium thiocyanate precipitation, ethanol fractionation and additional potassium thiocyanate precipitation.

Typical preparations of PIF are described by K. E. Mogensen and Kari Cantell in Pharmac. Ther. A., Vol. 1, pp 369–381, 1977.

"PIF-B", that is "partially purified interferon type B" is a product which contains less contaminating proteins than PIF, and which is typically prepared by employing, in the last stage of the potassium thiocyanate precipitation, a pH decrease to only 4.7 instead of a pH decrease to 3.0. Further details concerning this typical preparation appear from K. E. Mogensen and Kari Cantell, idem.

The invention also relates to pharmaceutical preparations for parenteral administration in human beings, the said preparations containing porcine leucocyte interferon as the active component. These pharmaceutical preparations contain the porcine leucocyte interferon in a form which is tolerable by human beings on parenteral administration, that is, the porcine leucocyte interferon fulfils the above-stated requirements to the effect that in immunoelectrophoreses, it does not show bands which are not identical with bands in human leucocyte interferon or human agammaserum, when antitotal human serum protein, antihuman IgG, antihuman IgA, anithuman IgM, antihuman albumin and antihuman leucocyte interferon are used as pecipitating antibody, apart from any bands originating from the medium in which a biological interferon inductor has been propagated. Preferred pharmaceutical preparations contain the porcine leucocyte interferon in the form of PIF fulfilling the above-stated conditions with respect to immuno-electrophoretical behaviour. The administration of this pharmaceutical preparation of the invention is adapted to the particular clinical case dependent upon whether for example treatment of cancer or of a virus infection is concerned, or of hepatites which are presumably also caused by virus. A guideline for the administration for treating cancer, papillomas, virus diseases and hepatites is administration of 2.5–8 millions of international units parenterally, for example intramuscularly or subcutaneously, per day for 30 days and thereafter 2.5–8 millions of international units three times per week for up to 1½ year. Another aspect of a pharmaceutical preparation according to the invention is eye drops containing porcine leucocyte interferon, also preferalby in the form of PIF. Such eye drops are for example indicated for Herpes keratitis. Eye drops containing interferon should contain a high titer as only small amounts can be applied. An application intraspinally is the use of the porcine leucocyte interferon in the form of PIF indicated for virus encephalitis, dissiminated sclerosis and tumors in the CNS system. Here, the use of the same dosages as stated above is preferred. However, in this case, the administration need not be performed so frequently, as the interferon leaves the CNS system more slowly than it leaves the remaining part of the organism. Finally, it is contemplated that the porcine leucocyte interferon can be used in nasal sprays for treating colds, such as illustrated in the literature for human interferon, and in the same administration amounts as stated in the literature for this purpose. If one does not use one of the standard administrations mentioned, one can individualize the treatment by measuring, subsequent to the administration of interferon, the interferon titer in the serum or body fluids of the patient. According to the literature, one should here aim at a titer of 50–100 international units per ml during the first minutes to hours after intramuscular injection, or during the first minutes subsequent to intravenous administration (on intravenous administration, the activity curve will fall steeply (exponentially) already during the first minutes).

As indicated above, the porcine leucocyte interferon according to the invention with the stated properties with respect to human tolerance is obtained by avoiding, during the total preparation procedure, that is, harvesting, isolating, priming, induction and incubation of the porcine leucocytes for the interferon production, the addition of protein sources which are not tolerable to human beings. This is obtained by using, as added protein source in any of the above-mentioned stages, a protein source which fulfils the above-mentioned requirements. The preferred protein sources fulfilling the above-mentioned requirements are porcine agammaserum and porcine albumin which may be prepared according to methods known per se such as illustrated in the below examples.

The fact that porcine aggammaserum and fractions thereof, including especially porcine albumin, and porcine hemoglobin from hemolyzed erythrocytes do not, in immunoelectrophoreses using the above-mentioned antibodies, show bands which do not appear in human serum, is utilized in another aspect of the invention. This aspect is constituted by such processes for or in preparing protein-containing pharmaceutical preparations for parenteral administration in human beings, in which cells or tissue are grown in a nutrient medium containing a protein source, and a material produced by the cells or cultured on the cells is obtained and optionally further purified, this aspect of the invention being characterized in using, as protein source, porcine agammaserum or a fraction thereof, including especially procine albumin, or porcine hemoglobin originating from hemolyzed porcine erythrocytes. It will be understood that processes of this kind are all such processes in which for example vaccines for parenteral administration in human beings are prepared, for example polio vaccine, transfer factor, etc.

In the known art, either human serum or various non-human materials have been used for these purposes. However, the availability of human serum is limited by the number of donors, and non-human materials such as bovine albumin, foetal calf serum, etc. may give rise to hypersensitivity reactions in the patients. By using the porcine materials according to the invention, such hypersensitivity reactions are avoided, and the porcine materials are available in very considerable amounts.

Another aspect of the invention is the use of porcine albumin as plasma expander for shock conditions, instead of the human albumin or other plasma expanders previously employed. Also in this aspect, the invention utilizes the fact that porcine albumin is tolerated by human beings, and also, advantages are obtained with respect to the availability of a cheaper material in larger amounts than human albumin, and with respect to better tolerability than known non-human plasma expanders.

With respect to the above-mentioned aspects according to which porcine agammaserum, porcine albumin or porcine hemoglobin is used as added protein source for media in connection with the preparation of pharmaceutical preparations for parenteral use, it is to be noted that the principles utilized in connection with this aspect of the invention are the same as discussed in detail above in connection with the very important special embodiment thereof constituted by the preparation of porcine leucocyte interferon using as added protein source porcine agammaserum, porcine albumin or porcine hemoglobin.

With respect to the operational details, the preparation and purification of porcine leucocyte interferon may be performed fully analogously to the process described by K. E. Mogensen and Kari Cantell in Pharmac. Ther. A., Vol. 1, pp 369–381, 1977, such as is also illustrated in the below examples which at the same time illustrate a few minor, but substantial differences in comparison with the process described in the said literature reference: The use of Eagle's Minimum Essential Medium with Hank's salt instead of with Earle's salt, as it has been found that porcine leucocytes thrive better with Hank's salt than with Earle's salt, and the addition of a calcium and magnesium chelate-forming agent to avoid the otherwise considerable agglutination of the porcine leucocytes. A suitable calcium and magnesium chelate-forming agent has been found to be $K_2EDTA$.

As inductor in the process of the invention is preferably used Sendai parainfluenza 1 virus, which is an analogy with the methods according to Mogensen and Cantell, but in contrast to the preparations of porcine leucocyte interferon described in the literature. However, it is to be noted that when preparing the porcine leucocyte interferon, one should employ larger amounts of Sendai virus than when preparing human leucocyte interferon as described in the literature. Preferred added amounts of Sendai virus are 200–400 HA units per ml MEM/leucocyte mixture. The use of Sendai virus seems to be preferred, but also other interferon inductors of the various type well described in the literature may be used for preparing the porcine leucocyte interferon, including NDV virus (Newcastle disease virus), VSV virus (vesicular stomatitis virus) or Sendai Harris Virus.

Reference is now made to the drawing:

FIG. 1 shows a Grabar immunoelectrophoresis on agarose gel. In the upper hole, 10 mcl (mcl=microliter) human serum has been applied, in the middle hole, 10 mcl human serum has been applied, and in the lower hole, 10 mcl human agammaserum has been applied. The electrophoresis has been run at 150 volts for 90 minutes. Thereafter, rabbit antihuman total serum protein has been applied in the upper groove, and in the lower groove has been applied rabbit antihuman IgA. Traces of IgA corresponding to the application site for agammaserum are noted.

Figure 2:
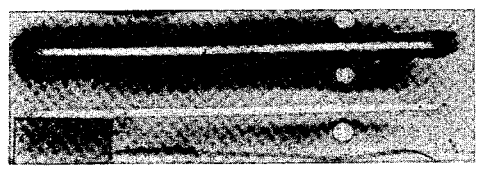

FIG. 2 shows a Grabar immunoelectrophoresis on agarose gel. In the upper hole, 10 mcl human serum has been applied, in the middle hole, 10 mcl human serum has been applied, and in the lower hole, 10 mcl human agammaserum has been applied. The electrophoresis has been run at 150 volts for 90 minutes. Thereafter, rabbit antihuman total serum protein has been applied in the upper groove, and rabbit antihuman IgM has been applied in the lower groove. Traces of IgM around the application site for human agammaserum are noted.

Figure 3:
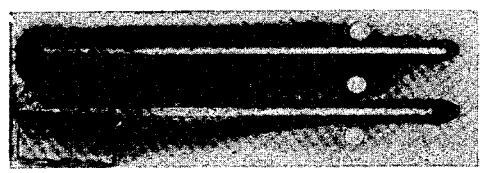

FIG. 3 shows a Grabar immunoelectrophoresis on agarose gel. In the upper hole, 10 mcl human serum has been applied, in the middle hole, 10 mcl porcine serum has been applied, and in the lower hole, 10 mcl human serum has been applied. The electrophoresis has been run at 150 volts for 90 minutes. Thereafter, rabbit antihuman total serum protein has been applied to the upper groove, and in the lower groove, rabbit antihuman IgG has been applied. Identity between human serum and porcine serum with respect to IgG is noted, as there is fusion at the ends of both upper and lower grooves. In addition, substantially identical migration of precipitating proteins originating from, on the one hand, human serum and, on the other hand, the porcine serum will be noted.

Figure 4:
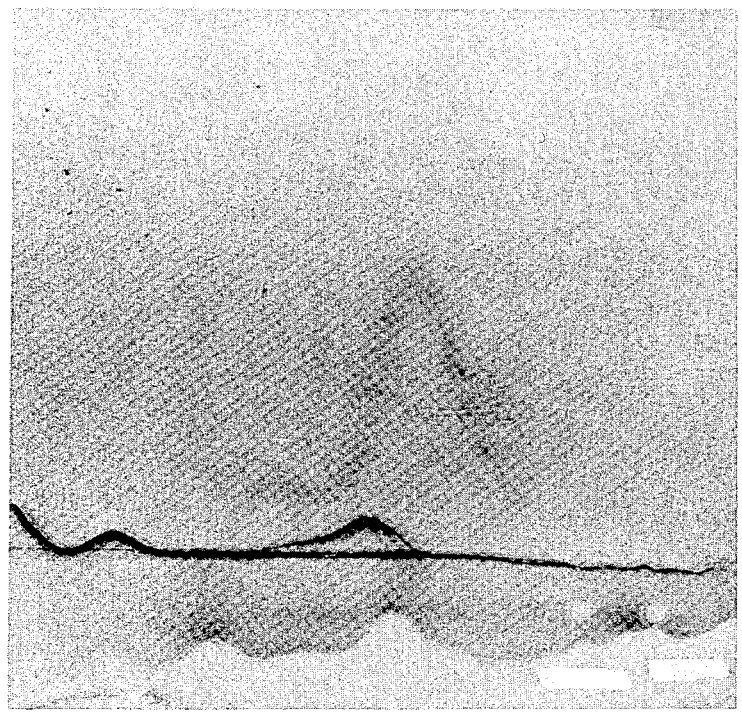

FIG. 4 shows tandem crossed immunoelectrophoresis, modified according to Freeman. In the application hole to the extreme right has been applied 10 mcl human serum, and on the application site to the left thereof has been applied 10 mcl porcine plasma. The electrophoresis has been run at 150 volts for 120 minutes, whereafter the electrophoresis slab has been cut out and placed against an agarose gel containing 0.75 mcl rabbit antihuman albumin per cm$^2$. Thereafter, the electrophoresis has been run perpendicular to the length of the slab for 18 hours at 60 volts. In the left part of the figure, the two precipitates of albumin originating from porcine plasma and human serum, respectively, are seen to be identical. In addition, in the middle of the figure, a diffuse precipitate is seen, consisting of two peaks, one of which is considerably higher than the other one. This diffuse precipitate represents albumin-bound protein. Identity between the small peak originating from porcine plasma and the high peak originating from human serum is noted. In addition, under the diffuse peaks, a clear precipitate is noted which also consists of two fused precipitates (where it is difficult to distinguish between the two peaks). These more clear peaks represent albumin-bound protein. No crossings are noted between these two peaks.

Figure 5:
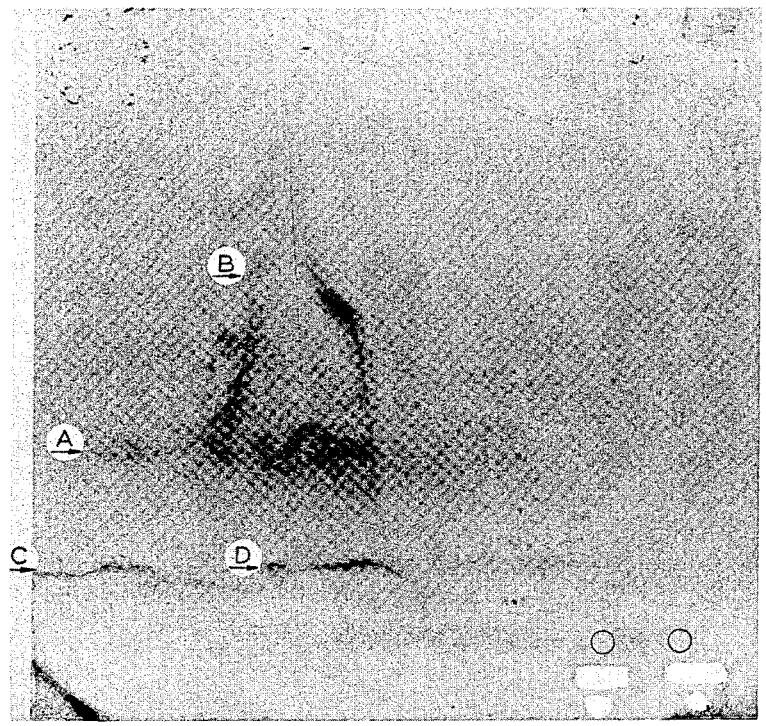

FIG. 5 shows a tandem crossed immunoelectrophoresis of the same kind as shown in FIG. 4. In the application hole to the extreme right, 20 mcl PIF-H has been applied, that is, human "partially purified interferon", and in the application hole to the left thereof, 20 mcl PIF-P has been applied, that is, porcine "partially purified interferon". The electrophoresis has been run as described in connection with FIG. 4. As antibody has been used rabbit antihuman total serum protein in a concentration of 4.0 mcl/cm$^2$. In total four double bands, marked with A, B, C, and D, respectively, will be noted. There is complete identity between on the one hand PIF-P and on the other hand PIF-H corresponding to these four precipitations.

Figure 6:
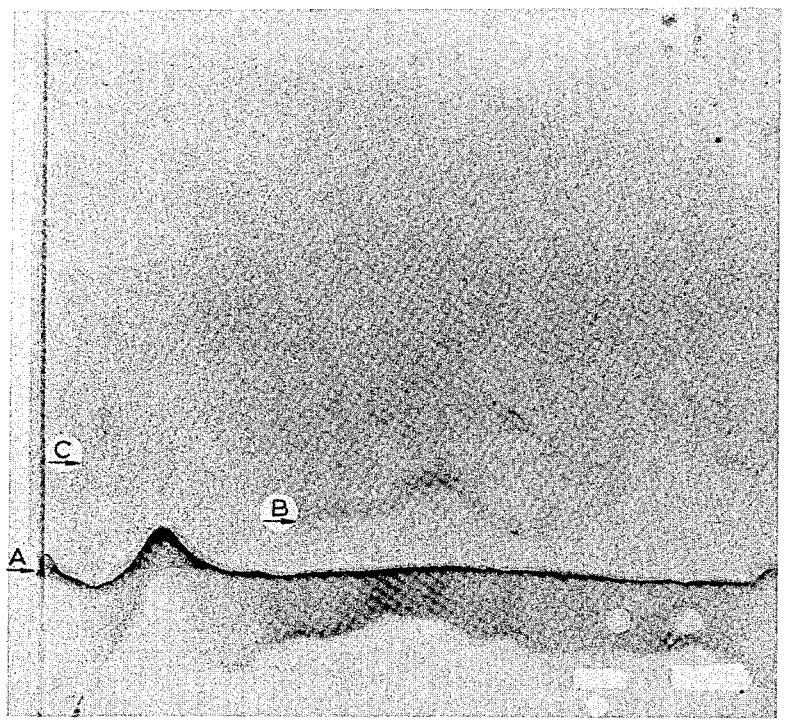

FIG. 6 shows a tandem crossed immunoelectrophoresis of the same kind as shown in FIG. 4. In the application hole to the extreme right has been applied 20 mcl PIF-H, and in the application hole to the left thereof has been applied 20 mcl PIF-P. The electrophoresis has been run in the same way as described in connection with FIG. 4, and as antibody has been used rabbit antihuman albumin in a concentration of 0.75 mcl/cm$^2$. As marked with A, identity between albumin from PIF-P and albumin from PIF-H will be noted. Corresponding to B will be noted identity between albumin-bound protein from PIF-P and PIF-H, respectively. Corresponding to C will be noted a single diffuse precipitate originating from egg albumin which is present in larger amounts of PIF-H, and which originates from the allantois liquid in which the Sendai virus used as interferon indicator has been propagated. (By Laurell rocker electrophoresis it has been ascertained that the same portion of PIF-H contains considerably larger amounts of egg albumin. In PIF-P, the same Laurell rocket electrophoresis showed only a small diffuse precipitate which migrated a little farther than the remaining albumin present in PIF-P.)

FIG. 7 and FIG. 8 show polyacrylamide gradient gel-electrophoreses (PAGE) run in SDS. In each figure, molecular markers are applied on the right slab with (starting from the bottom) molecular weight 12,000, (1); 17,800, (2); and 25,000 (3). In addition there is, on the molecular markers, indicated albumin (45,000), (4); and furthermore a molecular marker at 67,000, (5). The left slabs of both FIG. 7 and FIG. 8 show PIF-H (FIG. 7) and PIF-P (FIG. 8), respectively. Corresponding to PIF-P will be noted indications for molecular weight 12,400, 17,800, and 25,000. The same molecular weight markers can be plotted into FIG. 7. FIG. 9 shows the same type of gradient electrophoresis with the same molecular markers on the right slab, but with a known PIF-H preparation (donation from Kari Cantell, cf. Pharmac. Ther. A., Vol. 1, pp 369–381, 1977). There will be noted substantially identical distribution of the protein bands between the three different PIF's which are shown in FIG. 7, FIG. 8, and FIG. 9, respectively.

EXAMPLE 1

Preparation of porcine leucocyte interferon using human serum as added protein

A. Preparation of buffy coats (1) Blood was collected when slaughtering Danish Landrace pigs having a body weight of about 90 kg. After anaesthetization, the necks were washed with sodium hypochlorite solution, and the pricking and draining were performed with sterile tube knives through sterile polyamide hoses into polypropylene bottles containing 600 ml of ACD-citrate. From each pig, 2.5–3.0 liter blood was drained. The blood was carefully mixed with the citrate solution and thereafter cooled to 4° C. In total, blood from 12 pigs was drained.

(2) The cooled, stabilized pig blood was transferred under sterile conditions into 500 ml glass infusion bottles which were centrifuged for 20 minutes at 2100 rpm at 4° C. From each 500 ml bottle, the plasma layer was suctioned off, and thereafter, 15–20 ml leucocyte/erythrocyte mixture was transferred into a sterile 100 ml measuring cylinder. Buffy coats from all 12 pigs were pooled. The cylinder glasses were kep overnight at 4° C.

B. Preparation of crude interferon

The total amount of buffy coats (1260 ml) was treated with 9 liters of 0.83% ammonium chloride solution for 10 minutes at 4° C.

The buffy coat/NH4Cl mixture was centrifuged in Damon/IEC basket centrifuge at 3500 rpm with a feed of 500 ml per minute. The supernatant in the centrifuge bowl was suctioned off, and the leucocyte layer was resuspended in 200 ml Dulbecco's PBS without Ca and Mg, admixed with 0.5% dipotassium EDTA. Thereafter, the treatment was repeated with 0.83% NH4Cl solution (10 minutes at 4°C.), and the mixture was centrifuged in cooling centrifuged at 800 rpm at 4° C. for 25 minutes. The supernatant was suctioned off, and the leucocytes were suspended in 50 ml Eagle's Minimum Essential Medium with Hank's salt admixed with 9% of human serum from which gammaglobulins had been precipitated with $(NH_4)_2SO_4$ and which had a protein concentration of 2400 mg/100 ml. The medium had in addition been admixed with 3 mg tricine and 25 μg neomycin per ml. The leucocyte concentration in the medium was adjusted to $10^7$ cells per ml by adding additional medium.

The MEM leucocyte mixture was distributed in six 2000 ml round flasks, each containing 930 ml. To each flask was added 0.6 ml human raw concentrated leucocyte interferon containing 160,000 international interferon units per ml. Hence, the end concentration was 100 international units of interferon per ml MEM leucocyte mixture. The flasks were applied on water bath at 37.5° C. with wing magnet stirring and were loosely covered with aluminum foil. 2 hours later, 49 ml of Sendai virus suspension containing 8000 HA units of virus per ml were added to each flask. The incubation of water bath was continued for additionally 18 hours. Thereafter, the contents of the flask were centrifuged at 2000 rpm at 4° C. for 40 minutes. The supernatant, which is the raw interferon, was frozen at −40° C. subsequently to withdrawal of 1 ml per flask for titer determination.

C. Concentration and purification into porcine "partially purified interferon" (PIF-P)

The crude interfron (5500 ml) was precipitated at pH 3.50 in the presence of 0.5 M KSCN. The precipitate was dissolved in 1100 ml 95% ethanol at −20° C. and pH 4.45. Thereafter, the pH was increased stepwise, first to 5.45. The precipitate was discarded. The pH was increased to 5.80, and an additional precipitate was removed. Thereafter, the pH was increased to 8.00, and the new precipitate, containing the major amount of interferon, was dissolved in 110 ml of phosphate buffer at pH 8.00. On the following day, interferon and other proteins were again precipitated at pH 3.00 in the presence of 0.5 M KSCN. The precipitate was redissolved in 6 ml of Dulbecco's PBS, and the pH of the solution was adjusted to 7.82 by adding 0.075 ml 2 N NaOH. The solution was transferred to a dialysis hose and dialyzed against 1000 ml PBS. The dialysis liquid was changed after 24 hours, and after additional 24 hours of dialysis, the solution was centrifuged for 60 minutes at 25,000 rpm and 2° C. The supernatant is the final PIF-P.

Bacteriological investigation was performed by seeding 0.1 ml on the surface of Brain Heart Infusion agar (Difco) admixed with 5% defirinated horse blood, followed by aerobic and anaerobic incubation for 3–4 days at 37° C. No growth was noted on the plates.

EXAMPLE 2

Preparation of porcine leucocyte interferon using porcine serum as added protein A. Preparation of porcine agammaserum ACD-stabilized pig blood, drained and treated as described in Example 1 A (1), was centrifuged at 2500 rpm. at 4° C. for 7 minutes. The plasma layer was suctioned off. 11.2 ml of calcium chloride solution (10%) per 100 ml plasma was added. The plasma was put on water bath, 37.5° C., for coagulation. Thereafter, the plasma was allowed to stand for 18 hours at 4° C. The plasma thus converted into serum was centrifuged at 3500 rpm for 40 minutes at 4° C. To a 10 liter portion of the thus prepared porcine serum, 5385 ml of icecold saturated ammonium sulphate solution was added with stirring. This corresponds to 35%'s saturation with ammonium sulphate, whereby inter alia the gamma-globulins prepcipiated. The mixture of the liquid and the precipitate was centrifuged at 2500 rpm for 10 minutes at 4° C. The supernatant was agammaserum. This agammaserum was dialyzed against cold physiological salt solution (10 times the volume) for 48 hours with two shifts in refrigerator. The pH value was adjusted to 7.4. Thereafter, the agammaserum was sterile-filtered through Sartorius-filter with the smallest pore size, 0.22μ. The agammaserum was poured into sterile 500 ml bottles with sterile screw cap. Bacteriological determination was performed in the same way as described for PIF-P in Example 1. Thereafter, zone electrophoresis on cellulose acetate and determination of the protein concentration were performed. The agammaserum was adjusted to a protein concentration of about 2500 mg/100 ml by means of sterile physiological saline.

B. Thereafter, the preparation of crude interferon and purification of the interferon were performed in exactly the same manner as described in Example 1, but using, instead of the human serum, each time the same amount of the porcine agammaserum prepared in the manner described above.

The determinations illustrated on the Figures were performed on a production of PIF-P, the preparation of which was performed using 5 parts of crude interferon prepared as described in Example 1 and 1 part of crude interferon prepared as described in the present example.

EXAMPLE 3

Preparation of porcine albumin

To porcine plasma, drained and treated as in Example 1 A (1) was added 12% w/v PEG 4000 (polyethylene glycol with molecular weight 4000) in solid form at pH 8, whereby the major part of the plasma proteins with high molecular weight such as lipoproteins and fibrinogen as well as IgG were precipitated. The resulting mixture of liquid and precipitate was centrifuged at 2500 rpm for 10 minutes at 4° C. The albumin amount in the supernatant was determined by Laurell rocket electrophoresis. Thereafter, pH was lowered to 4.6, and additional solid PEG 4000 was added until 25% w/v saturation had been obtained. Thereby, the albumin was precipitated. The mixture of liquid and precipitate was centrifuged at 2500 rpm for 10 minutes at 4° C. The precipitate was washed with glass-distilled water at 4° C. Thereafter, Dulbecco's PBS buffer (pH 7.3, minus Ca and Mg) was added until an albumin concentration of four times the concentration measured by the above-mentioned Laurell rocket electrophoresis. With magnet stirring, 0.1 N sterile sodium hydroxide solution was added to pH 7.0.

The albumin thus redissolved was applied on a DEAE Sephadex ® A50 ion exchanger column equlibrated with the above-mentioned Dulbecco PBS buffer, adjusted to pH 7.0. Thereafter, the pH in the column was adjusted to 4 by addition of citrate buffer, ionic strength 0.07. Albumin was eluted at pH 4.6. With stirring, 5 M potassium thiocyanate solution was added to the eluate in such an amount that the end concentration became 0.5 M. The pH was lowered to 3.5, whereby albumin was precipitated. The supernatant was removed by centrifugation at 2000 rpm for 25 minutes at 2° C. The precipitate was resuspended with Dulbecco's PBS buffer (pH 7.3, minus Ca and Mg) to an albumin concentration corresponding to 4 times the value measured by Laurell rocket electrophoresis as described above. The pH was adjusted to 7.3 with cold sterile sodium hydroxide solution, and thereafter, the solution was poured into a dialysis hose and dialyzed for 2 days against a 100 times larger volume of Dulbecco's PBS buffer (pH 7.3, minus Ca and Mg) at 4° C. with exchange of the dialysis liquid with fresh dialysis liquid after about 24 hours. Through this, potassium cyanate was removed from the solution. The final albumin concentration was measured by Laurell rocket electrophoresis. The purified albumin solution thus obtained was sterile-filtered through a Sartorius filter in which the smallest pore measure is 0.22μ. The resulting sterile albumin solution is suitable as protein addition in the preparation of porcine PIF, human PIF and PIF prepared from lymphoblastoid cells such as Namalva cells, as plasma expander for intravenous administration in human beings, as albumin stabilizer in parenteral preparations and as protein addition for culturing media for use in the preparation of parenteral biologically active preparations from cell/tissue cultures.

EXAMPLE 4

Determination of the titer of porcine interferon.

The following method is employed: A monolayer of Human Embryonal Lung cells (HEL) is incubated with the interferon sample in question (in various dilutions, for example a three-fold series dilution is performed) overnight. On the next day, the interferon sample is removed and replaced with a virus solution (Vesicular Stomatitis Virus, VSV) of predetermined strength. On the next day, the titrations are read according to the following principle: The cells which have "received sufficient" interferon will not be destroyed by VSV, while the cells which have received no (or very little) interferon will be destroyed. By following a dilution series of a particular sample, one can easily determine where the shift is positioned. The end point of the titration is defined as the dilution of the interferon sample which just gives 50% protection of the cell layer. This principle is described, for example, by Finter, N. (ed.): Interferon and Interferon Inducers (1973); Finter, N.: The Assay and Standardization of Interferon and Interferon Inducers. Two methods have been used: (A) The micro method, and (B) the "semi-macro" method.

Routinely, A is used as this method is relatively less laborious than B. Plastic trays (96 "flat" holes) are seeded with cells, etc. On each micro tray, there is always included an internal laboratory standard. This reference is compared once a month with the international reference standard (69/19B), so that all determinations are invariably stated in 69/19B units, which is the standard procedure for interferon laboratories (Finter, loc.cit.).

In method B, test tubes (WR glass) with rubber stoppers are used. The amount of cells per monolayer is about 10 times larger than in A. If very exact determinations are to be performed, B is used, as the uncertainty on a single determination is considerably less in method B than in method A. In both A and B, also a "crude concentrated interferon sample" from professor Kari Cantell (Cantell-CIF 500,000 IFU/ml) is included as control. Normally, there is always full conformity between the three "references" (the internal laboratory standard 4, 69/19B, Cantell-CIF).

On each of 5 incubation flasks, each containing 980 ml of crude interferon, prepared as described in Example 1 B (after the centrifugation and prior to the freezing), a titer determination has been performed according to the above-described method A: The following titers have been obtained (in international units of interferon):

Flask 1: 40,000
Flask 2: 50,000
Flask 3: 36,000
Flask 4: 25,000
Flask 5: 120,000

On a flask with 980 ml of crude interferon, prepared as described in Example 2 B, that is, the corresponding material as in Example 1, but prepared using porcine agammaserum, the titer was found to be: 109,000 international interferon units.

A determination of PIF activity in the same manner showed a concentration of the order of 100-fold. During the concentration and purification procedures, a loss of 50–80% interferon activity is encountered, calculated in relation to the above-mentioned titer. It is noted that in the titer determination on the porcine interferon, there was no sign of any cytotoxic effect on the human cells.

Porcine interferon was also prepared as described in Examples 1 and 2, but using other virus inductors including NDV Hitchner and NDV Tokyo. It was found that NDV Hitchner does not induce porcine interferon, but that with employment of 50, 70, and 100 HA units, respectively, of NDV Tokyo, a titer of 10,000 international units of interferon was obtained in human test cell systems as described above.

EXAMPLE 5

Neutralization of porcine interferon with antihuman leucocyte interferon produced in sheep Porcine leucocyte interferon cross-reacts partially (up to about "25%") with antihuman leucocyte interferon (antiserum produced in sheep by means of PIF-H).

In principle, the following is done: (1) Firstly, the titer of the porcine interferon in the human system is determined as described in Example 4. (2) Thereafter, the neutralization test proper is performed (also in the human system).

(Ad 1). A three-fold series dilution of P-019-3 (a crude interferon batch prepared as described in Example 1B, is performed, starting from for example 1:1000 (thereafter 1:3000, etc.). These dilutions are incubated on micro trays (which have previously been seeded with 30,000–40,000 human cells) until the next day, whereafter the dilutions are replaced with a VSV solution (Vesicular Stomatitis Virus) of a predetermined strength. On the next day, the titrations are read according to the following principle: 50%'s protection of the cells is used as "end point". It was found that P-019-3 could be diluted 20,000 times and still give rise to 50%'s protection of the cells in dilution (1:3). In other words, the titer is 60,000 (in the system in question —HEL-cell system—69/19B unit=1 "lab. unit"=1 4/4 ref. 74-unit). Thus, one can prepare a solution of 3 procine units (in the human system) by first diluting 20,000 times and thereafter 3 times. P-019-3-solutions of 20, 10, and 5 porcine units/ml, respectively, were prepared. At the same time, corresponding interferon solutions of human leucocyte interferon (4/4 ref.-74): 20, 20, and 5 IFU/ml, were prepared.

(Ad 2). A Two-fold series dilution of antihuman leucocyte interferon, starting from 1:500 (1:1000, 1:2000 up to 1:1,024,000) was performed. To each antiserum dilution was added the same amount of porcine units of P-019-3 (0.5 ml P-019-3), corresponding to 20 units/ml+0.5 ml antihuman interferon (1:500), thereafter 0.5 ml P-019-3 (20 units/ml) +0.5 ml antihuman interferon (1:1000, etc. up to 1:1,024,000) was allowed to stand for 1 hour at 37° C. Thereafter, the mixture (1 ml) was tested for interferon activity in the human system as described above. 50%'s protection is taken as end point for the antibody titration. For example, the 1:16,000 dilution (of anti interferon serum) gave 50% protection of the cells when using 5 units of P-019-3. With units of human interferon (4/4 ref. -74), the shift appears only at 1:256,000. This means that porcine interferon (of batch P-019-3) cross-reacts with human interferon to an extent of about 10%.

Affinity chromatography

The above results with respect to neutralization were confirmed by an affinity chromatography using a Sepharose ® 4B CNBr column to which was coupled, and thereby immobilized, sheep anti PIF-H. When the porcine leucocyte interferon of batch P-019-3 was applied on the column and thereafter eluted about 25% of the original activity of the porcine leucocyte interferon was retained by the column, whereas about 75% of the original activity of the porcine leucocyte interferon was determined (in the manner described above) in the eluate.

EXAMPLE 6

Tolerance of PIF-P in human beings

In 5 volunteers, the same PIF-P as is characterized in the Figures was injected intramuscularly (1 ml). Prior to the injection of PIF-P a blood sample was withdrawn. 8 days subsequent to the administration of PIF-P, a blood sample was again withdrawn. The two blood samples withdrawn from each patient were tested for precipitating antibodies against PIF-P by Ouchterlony immunodiffusion. No precipitates were found. To 3 of the 5 volunteers, an additional booster injection of PIF-P was adminstered intramuscularly (1 ml) after an interval of 14 days. No side effects were found, especially no hypersensitivity reaction.

EXAMPLE 7

Production of human lymphoblastoid interferon (Namalva).

Namalva cells were cultivated at RPMI 1640 medium admixed with 15% human agammaserum. The cells were propagated as described by Strander et al., J. Clin. Microbiol., Vol. 1, 116–117, 1975. In the production of the lymfoblastoid interferon, 150 HA units of Sendai virus per ml medium were used as inductor. The process for preparing the lymphoblastoid interferon from the cultivating medium was also performed as described by H. Strander et al., loc. cit., apart from the fact that in the incubation medium, there was used, instead of foetal calf serum, human agammaserum in the same amount. Hereby, titers of about 45,000 international units of interferon per ml have been obtained.

The human agammaserum may be substituted wholly or partially with porcine agammaserum or porcine albumin, prepared as described in Example 2 and 3, respectively.

In accordance with this example, an aspect of the present invention comprises preparing human lymphoblastoid interferon by cultivating human lymphoblastoid cells, using as added protein source for the cultivation human agammaserum, human agammaplasma, human albumin, human hemoglobin from hemolyzed erythrocytes, porcine agammaserum, porcine agammaplasma, porcine albumin or porcine hemoglobin from hemolyzed erythrocytes, treating the cells with an interferon inductor, incubating them and obtaining the resulting interferon, using as added protein source for the incubation porcine agammaserum, porcine agammaplasma, porcine albumin or porcine hemoglobin from hemolyzed erythrocytes (the use of human agammaserum for the incubation of human lymphoblastoid cells is described by Kari Cantell (Ann.N.Y.Acad. Sci., Vol. 173, pp 160–168, 1970)).

What we claim is:

1. A process for preparing exogenic porcine leucocyte interferon which shows antiviral protective activity in human cells comprising:
   harvesting and isolating porcine leucocytes:
   treating said porcine leucocytes with an interferon inductor;
   incubating said treated porcine leucocytes;
   adding a protein source which in immunoelectrophoreses is substantially composed of bands which are identical or partially identical with corresponding bands in human agammaserum when using, as precipitating antibody, antitotal human serum protein, antihuman IgG, antihuman IgA, antihuman IgM or antihuman albumin.

2. The process of claim 1, wherein the porcine leucocyte is primed.

3. A process according to claim 1 in which the protein source is selected from the group consisting of human agammaserum, human agammaplasma, human albumin, human hemoglobin from hemolyzed erythrocytes, porcine agammaserum, porcine agammaplasma, porcine albumin, and porcine hemoglobin from hemolyzed erythrocytes.

4. The process of claim 3, wherein the protein source is porcine agammaserum and agammaplasma.

* * * * *

UNITED STATES PATENT AND TRADEMARK OFFICE
CERTIFICATE OF CORRECTION

PATENT NO. : 4,273,703
DATED : June 16, 1981
INVENTOR(S) : Kurt B. Osther, et al It is certified that error appears in the above—identified patent and that said Letters Patent is hereby corrected as shown below:

Column 5, line 19, "preferalby" should read -- preferably--.

Column 9, line 49, "incubation of" should read -- incubation on--.

Column 10, line 11, "defirinated" should read -- defibrinated --.

Column 13, line 18, "-69/19B" should read -- 1 69/19B --.

Column 13, line 24, "20, 20, and 5" should read -- 20, 10, and 5 --.

Signed and Sealed this

Seventeenth Day of November 1981

[SEAL]

Attest:

GERALD J. MOSSINGHOFF

Attesting Officer

Commissioner of Patents and Trademarks